Figure 1B:
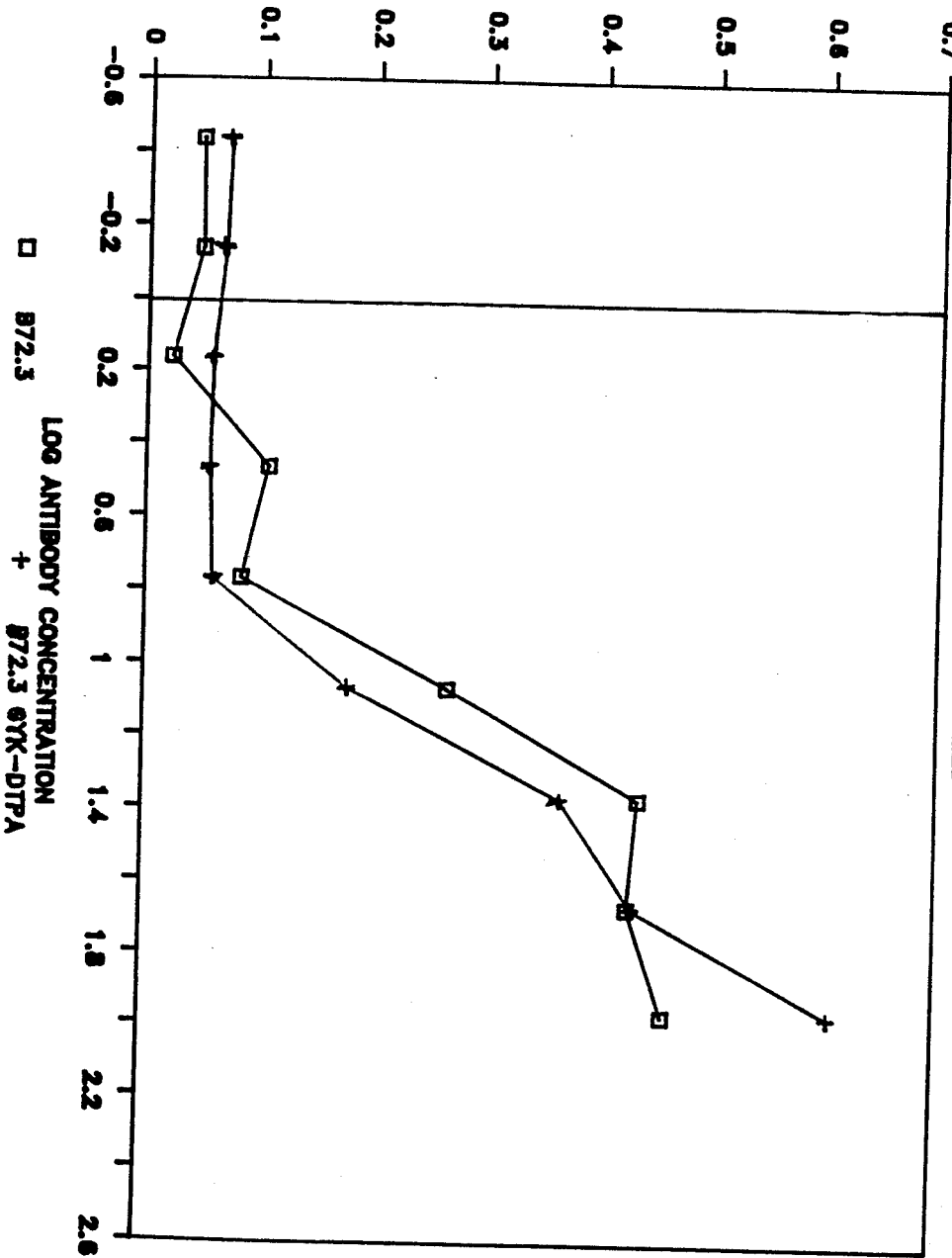

| United States Patent [19] | [11] Patent Number: 4,937,183 |
| Ultee et al. | [45] Date of Patent: Jun. 26, 1990 |

[54] METHOD FOR THE PREPARATION OF ANTIBODY-FRAGMENT CONJUGATES

[75] Inventors: Michiel E. Ultee, Belle Mead, N.J.; Vernon L. Alvarez, Morrisville, Pa.

[73] Assignee: Cytogen Corporation, Princeton, N.J.

[21] Appl. No.: 152,209

[22] Filed: Feb. 3, 1988

[51] Int. Cl.$^5$ .................. C12P 21/06; G01N 33/563; C07K 15/28; A61K 49/00

[52] U.S. Cl. .................. 435/68.1; 435/188; 435/272; 436/512; 436/547; 436/548; 935/107; 530/388; 530/389; 424/9

[58] Field of Search .......... 435/7, 23, 68, 69, 188, 435/262, 272; 436/512, 547, 543, 544, 545, 548; 935/107; 530/388, 389; 424/85, 9, 1.1

[56] References Cited

U.S. PATENT DOCUMENTS

| 4,331,647 | 5/1982 | Goldenberg | 424/1 |
| 4,671,958 | 3/1986 | Rodwell et al. | 424/85.91 |
| 4,814,433 | 3/1989 | Fredrickson | 530/388 |

FOREIGN PATENT DOCUMENTS

86/01410  3/1986  World Int. Prop. O.
86/01720  3/1986  World Int. Prop. O.

OTHER PUBLICATIONS

Parham, P., et al., *J. Immunol. Methods*, 53: 133–173 (1982).
Parham, P., *J. Immunol.*, 131:2895–2902 (1983).
Goodman, J. W., "Immunoglobulins I: Structure and Function", in *Basic and Clinical Immunology*, Lange Medical Publications, Los Altos, Calif. (Stites et al., ed.) pp. 30–36 (1982).

*Primary Examiner*—Esther M. Kepplinger
*Assistant Examiner*—Toni R. Scheiner
*Attorney, Agent, or Firm*—Pennie & Edmonds

[57] ABSTRACT

A novel method for preparing soluble antibody fragment compositions having superior characteristics for targeted delivery when administered in vivo are disclosed. The antibody fragment compositions are characterized by substantially the same immunospecificity as the unconjugated antibody and aqueous solubility such that they are suitable for in vivo administration. Therapeutic and diagnostic methods utilizing the antibody fragment compositions are also disclosed.

24 Claims, 3 Drawing Sheets

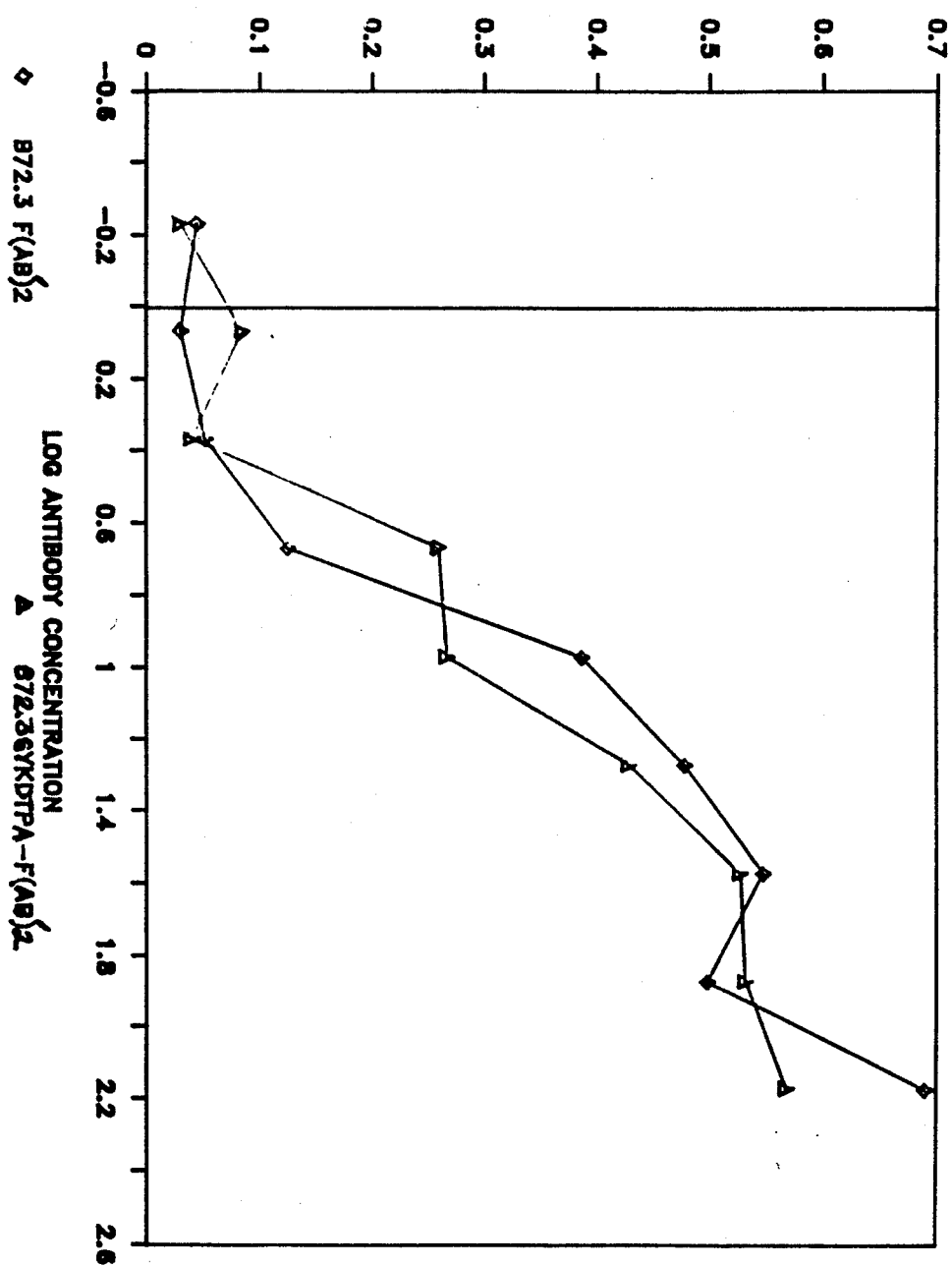

4,937,183

METHOD FOR THE PREPARATION OF ANTIBODY-FRAGMENT CONJUGATES

1. FIELD OF THE INVENTION

The present invention is directed generally to the area of antibody systems for the delivery of compounds to target sites in vivo. More particularly, the invention is directed to novel methods for preparing conjugates comprising an antibody fragment site specifically attached to a compound via an oxidized carbohydrate moiety of the antibody fragment The compositions prepared according to the method of the invention are advantageously employed to deliver compounds to target sites following in vivo administration.

2. BACKGROUND OF THE INVENTION

U.S. Pat. No. 4,671,958 issued to Rodwell et al. describes a method for site specific covalent attachment of a compound to an antibody molecule by selectively oxidizing a carbohydrate moiety of the antibody, located outside the antigen binding region of the antibody, to form an aldehyde group and then reacting the resultant aldehyde group with an amine group such as a primary amine, secondary amine, hydrazine, hydrazide, hydroxylamine, phenylhydrazine, or semicarbazide to form an antibody-compound conjugate which is characterized by substantially the same immunospecificity as the unconjugated antibody.

European Patent Application No. 85401695.3 published March 5, 1986 describes methods for preparing and compositions comprising aqueous soluble antibody-metal ion complexes in which a compatible chelator coordinately bound to a metal ion is covalently attached via an amine group of the chelator to an oxidized carbohydrate moiety of an antibody molecule, located outside the antigen binding region of the antibody. The antibody-metal ion complexes are characterized by (1) substantially the same immunospecificity as the unconjugated antibody molecule; and (2) aqueous solubility such that they are suitable for in vivo administration.

European Patent Application No. 85401776.1 published March 26, 1986 describes methods for preparing and compositions comprising aqueous soluble antibody-therapeutic agent conjugates in which a therapeutic agent is attached, either directly or through a linker, via an amine group to an oxidized carbohydrate moiety of an antibody molecule, located outside the antigen binding region of the antibody. The antibody-therapeutic agent conjugates are characterized by (1) substantially the same immunospecificity as the unconjugated antibody molecule; and (2) aqueous solubility such that they are suitable for in vivo administration.

The methods described in the above references involve site specific attachment of a compound to either a whole antibody molecule or a preformed antibody fragment such as a half antibody molecule (i.e., a single heavy: light chain pair), a Fab, a (Fab')$_2$, or a Fab' fragment to form the antibody-compound conjugates. Thus, according to conventional methods a preformed antibody fragment is coupled to a compound to form an antibody fragment conjugate.

In contrast, the present method involves cleavage of an antibody composition, comprising an antibody attached to a compound, a linker or a linker-compound intermediate, in which the attachment is site specific via an oxidized carbohydrate moiety of the whole antibody. Cleavage of the antibody composition according to the present invention forms an antibody fragment composition. The present invention is based on the surprising discovery that antibody fragment conjugates prepared according to the methods disclosed herein behave significantly different from conventional conjugates when administered in vivo and exhibit in vivo biodistribution which is advantageously used for targeted delivery to in vivo sites.

3. SUMMARY OF THE INVENTION

The present invention provides a novel method for the preparation of aqueous soluble antibody-fragment compositions as well as a unique class of antibody (Fab')$_2$ fragment compositions prepared by such method.

Surprisingly antibody fragment compositions prepared according to the methods of the invention when administered in vivo behave in a superior manner for targeted delivery when compared to analogous antibody fragment compositions prepared by conventional methods. Thus the present compositions are advantageously used for the targeted delivery of a wide variety of compounds for therapeutic and diagnostic applications.

In its most broad aspect, the present invention provides a method for preparing an antibody compound conjugate (antibody-linker intermediate) which comprises: reacting a soluble antibody-compound conjugate (antibody-linker intermediate), which comprises an antibody attached to a compound (linker-intermediate) by a covalent bond to an oxidized carbohydrate of the antibody located outside the antigen binding region of said antibody, with an activated thiol protease enzyme to form an antibody (Fab')$_2$ compound conjugate (antibody (Fab')$_2$-linker intermediate), characterized by (a) substantially the same immunospecificity as the unconjugated antibody and (b) aqueous solubility such that the antibody (Fab')$_2$ compound conjugate (antibody (Fab')$_2$-linker intermediate) is suitable for in vivo administration.

The invention also provides novel antibody (Fab')$_2$ compositions and methods utilizing such compositions for therapeutic and diagnostic treatment of a variety of cellular disorders.

4. BRIEF DESCRIPTION OF THE FIGURES

The present invention may be more fully understood by reference to the following detailed description of the invention, examples of specific embodiments and the appended figures in which:

FIGS. 1 (A-B) is a graphic illustration of the in vitro binding activity of B72.3 antibody compositions FIG. IA shows binding activity of a B72.3 (Fab')$_2$-linker intermediate prepared according to the reaction scheme described herein and of a conventionally prepared B72.3 (Fab')$_2$ fragment. FIG. 1B shows binding activity of a whole B72.3 linker intermediate and of the native whole B72.3 antibody.

Figure 2:
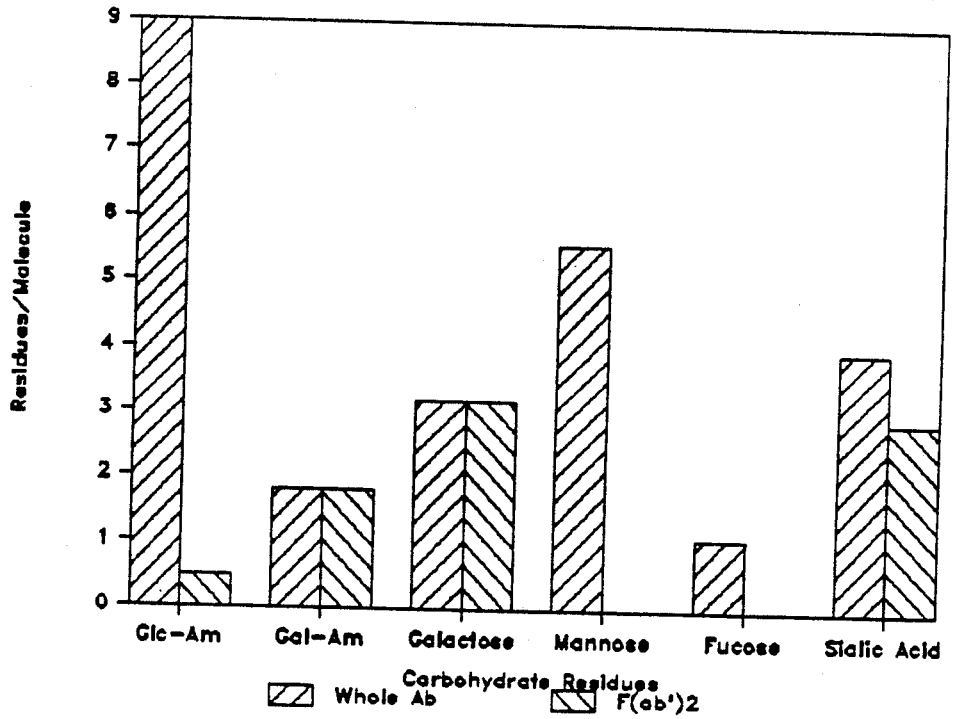

FIG. 2 is a representation of the carbohydrate moieties of B72.3 whole antibody and (Fab')$_2$ fragments.

5. DETAILED DESCRIPTION OF THE INVENTION

The present invention is directed to a novel method for preparing aqueous soluble antibody compositions, comprising an (Fab')$_2$ fragment of an antibody site specifically coupled to a compound either directly or via a linker. The antibody compositions are advantageously used for targeted delivery to an antigenic site in vivo. The invention is based on the surprising discovery that antibody compositions prepared according to the described method exhibit significantly different advantageous behavior and biodistribution when administered in vivo compared to analogous compositions prepared by conventional methods. In this application, the term (Fab')$_2$ is considered to be synonymous with the term F(ab')$_2$.

As used throughout this application, the term "antibody (Fab')$_2$" or "antibody (Fab')" is meant to include fragments of an antibody which are substantially the same in antigen binding activity and apparent molecular size or weight as those obtained using the pepsin digestion method described by Nisonoff et al., 1960, Arch. Biochem. 89:230. The (Fab')$_2$ fragments of the invention are not obtained using the pepsin digestion method of Nisonoff et al., supra. Rather they are prepared by digestion of an antibody-compound, an antibody-linker intermediate or antibody-linker-compound conjugate using a pre-activated thiol protease enzyme, including but not limited to papain, chymopapain, bromelain, ficin, etc. in the reaction scheme described herein. The antibody (Fab')$_2$ fragments do not exist as free (Fab')$_2$ fragments according to the invention, but rather as part of antibody (Fab')$_2$-compound conjugates, antibody (Fab')$_2$-linker intermediates or antibody (Fab')$_2$-linker-compound conjugates.

5.1. METHOD OF PREPARATION

Antibody (Fab')$_2$-compound conjugates are prepared by a method which results in a unique class of antibody fragment compositions different from any other previously described antibody fragment compositions Thus, according to the present invention antibody (Fab')$_2$-compound conjugates are prepared as follows:

An antibody-compound conjugate, an antibody-linker intermediate or an antibody-linker-compound conjugate is reacted with an effective amount of an activated thiol protease to form an antibody (Fab')$_2$ compound conjugate, an antibody (Fab') -linker intermediate or an antibody (Fab')$_2$-linker-compound conjugate. Suitable thiol protease enzymes include, but are not limited to: papain, chymopapain, bromelain, ficin, etc. The thiol protease enzymes are activated by reaction with cysteine or a low molecular weight sulfhydryl reducing agent such as dithiothreitol, mercaptoethanol, mercaptoethylamine, etc.

In practice, an antibody-compound conjugate, an antibody-linker intermediate or an antibody-linker compound conjugate is reacted with an amount of an activated thiol protease enzyme equivalent (on a weight basis) to about 1–20% of the antibody composition. The reaction mixture may be buffered using a buffer such as phosphate, citrate or acetate buffer at a pH from about 5.0–7.0, preferably pH 5.0–6.0. The reaction mixture is incubated at a temperature from about 4°–37° C, generally about room temperature (about 25° C). The reaction is preferably performed in the presence of a chelating agent such as, for example, ethylenediaminetetraacetic acid (EDTA) at about 1–3 mM, which enhances the stability of the thiol protease enzyme.

In practice, the thiol protease enzyme is preactivated by incubation with cysteine or a sulfhydryl reducing agent such as dithiothreitol, mercaptoethanol, mercaptoethylamine, etc. For example, a thiol protease enzyme may be activated by dissolving the enzyme at about 1 mg/ml in 50 mM oysteine-containing buffer and incubating the reaction mixture for about 1 hour at room temperature. The cysteine can be removed by gel filtration chromatography ("desalting") and then the eluted activated enzyme can be used as described to digest an antibody composition.

For convenience and ease of separation of the antibody (Fab')$_2$ compositions formed, the enzyme can be immobilized by attachment to a substrate such as agarose, Sepharose ® or Sephadex ®, polyacrylamide, or agarose-acrylamide beads, before activation. For example, agarose beads activated by reaction with carbonyldiimidazole (commercially available as "Reacti Gel Pierce" Chemical Corporation) can be used to immobilize the thiol protease enzyme employed in the present reaction scheme.

When an antibody-linker intermediate is used as the starting material, a compound is coupled to the antibody (Fab')$_2$ linker composition formed to form a useful antibody (Fab')$_2$-linker compound conjugate. When an antibodycompound conjugate or an antibody-linker compound conjugate is used as the starting material, the antibody (Fab')$_2$ compound conjugate formed is useful for a variety of in vivo applications.

The antibody (Fab')$_2$ compound conjugates prepared using the method of the invention are characterized by (1) substantially the same immunospecificity as the unconjugated antibody and (2) aqueous solubility such that they are suitable for in vivo administration.

The antibody-compound conjugates, antibody-linker intermediates and antibody-linker-compound conjugates used in the present invention are prepared according to methods described in United States Pat. No. 4,671,958 issued to Rodwell et al., in European Patent Application No. 85401695.3 published on March 5, 1986 and European Patent Appln. No. 85401776.1 published on March 26, 1986.

Briefly, a carbohydrate side chain of an antibody, located outside the antigen binding region of the antibody, is selectively oxidized or enzymatically modified to form an aldehyde group. The resulting aldehyde is reacted with an amine group (e.g., ammonia derivatives such as primary amine, secondary amine, hydroxylamine, hydrazine, hydrazide, phenylhydrazine, semicarbazide or thiosemicarbazide) to form a Schiff's base or reduced Schiff's base (e.g., imine, enamine, oxime, hydrazone, phenylhydrazone, semicarbazone, thiosemicarbozone or reduced forms thereof).

5.1.1. CHEMICAL METHODS OF OXIDATION

Oxidation of the carbohydrate portion or moiety of antibody molecules leads to formation of aldehyde groups. A variety of oxidizing agents can be used, such as periodic acid, paraperiodic acid, sodium metaperiodate and potassium metaperiodate. Among these, oxygen acids and salts thereof are preferred since secondary or undesirable side reactions are less frequent For a general discussion, see Jackson, 1944, In Organic Reactions 2, p.341; Bunton, 1965, Oxidation in Organic Chemistry, Vol. 1 (Wibert, ed.), Academic Press, New York, p.367.

Oxidation of the antibodies with these oxidizing agents can be carried out by known methods. In the oxidation, the antibody is used generally in the form of an aqueous solution, the concentration being generally less than 100 mg/ml, preferably 1 to 20 mg/ml. When an oxygen acid or a salt thereof is used as the oxidizing agent, it is used generally in the form of an aqueous solution, and the concentration is generally 0.001 to 10 mM and preferably 1.0 to 10 mM. The amount of the oxygen acid or salt thereof depends on the kind of antibody, but generally it is used in excess, for example, two to ten times as much as the amount of the oxidizable carbohydrate. The optimal amount, however, can be determined by routine experimentation.

In the process for oxidizing antibodies with oxygen acids or salts thereof, the optional ranges include a pH of from about 4 to 8, a temperature of from 0° to 37° C., and a reaction period of from about 15 minutes to 12 hours.

During the oxidation of the antibody with an oxygen acid or a salt thereof, light is preferably excluded to prevent over oxidation of the glycoprotein.

5.1.2. ENZYMATIC METHODS OF OXIDATION

Oxidation of the carbohydrate portion of antibody molecules may also be done with the enzyme, galactose oxidase (Cooper et al., 1959, J. Biol. Chem. 234:445–448). The antibody is used in aqueous solution, the concentration being generally 0.5 to 20 mg/ml. The enzyme generally is sued at about 5 to 100 units per ml of solution, at a pH ranging from about 5.5 to about 8.0. The influence of pH, substrate concentration, buffers and buffer concentrations on enzyme reaction are reported in Cooper et al., supra.

5.1.3. ATTACHMENT AND STABILIZATION

Antibody conjugates (or antibody linker-intermediates) are produced by reacting the oxidized carbohydrate portion of an antibody with a compound, a linker or a linker-compound having an available amine group selected from the group consisting of primary amine, secondary amine, hydrazine, hydrazide, hydroxylamine, phenylhydrazine, semicarbazide and thiosemicarbazide groups. The immediately resulting products contain a carbon-nitrogen double bond resulting from elimination of a molecule of water from the initial addition products:

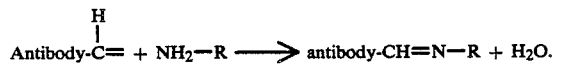

For a general discussion of the reaction of aldehydes with hydrazides, see March, 1978, In Advanced Organic Chemistry: Reactions Mechanisms and Structure, McGraw Hill Co., New York, pp. 824–825.

A solution of the oxidized antibody at a concentration of from about 0.5 to 20 mg/ml is mixed with a compound a linker or a linker-compound (molar ratios of reactive amine group to antibody aldehyde ranging from about 1 to about 10,000) and the solution incubated for from about 1 to 10 hours. Suitable temperatures are from 0° to 37° C. and pH may be from about 6 to 8.

After the antibody-conjugates (or antibody-linker intermediates) have been formed between the antibody and a compound, a linker or a linker-compound they can optionally be stabilized with a suitable reducing agent, such as sodium cyanoborohydride or sodium borohydride. Reducing agent is generally added to a molar excess of from about 10 to 100 fold molar excess over available aldehyde groups. For a general discussion, see Jentoft and Dearborn, 1979, J. Biol. Chem. 254:4359.

5.2. COMPOUNDS AND LINKERS

According to the invention, a compound can be site selectively attached to an oxidized carbohydrate moiety of an antibody directly through an amine group of the compound thus forming an antibody-compound conjugate.

Alternatively, a compound can be site selectively attached to an oxidized carbohydrate moiety of an antibody through an intermediate linker having at least two reactive groups, one an amine group to react with the oxidized carbohydrate moiety of the antibody and one to react with the compound. The linker, which includes any compatible compound, must be chosen such that the reaction with antibody (or compound) does not adversely affect antibody reactivity and selectivity. Moreover, if the compound attached is a therapeutic agent, such attachment must not destroy the activity of the therapeutic agent. Suitable linkers for reaction with oxidized antibodies include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

The compound can be attached to the linker before or after the linker is attached to the antibody molecule. In certain applications it may be desirable to first produce an antibody-linker intermediate in which the linker is free of an associated compound. Depending upon the particular application, a specific compound can then be covalently or coordinately attached to the linker.

Of additional interest are "branched linkers" which have multiple sites for attachment of compounds. For multiple site linkers, a single covalent attachment to an antibody or antibody fragment would result in an antibody-linker intermediate capable of binding a compound at a number of sites.

In another embodiment, cleavable linkers can be used which are susceptible to cleavage by a variety of mechanisms. Peptide linkers which are susceptible to cleavage by enzymes of the complement system, urokinase, tissue plasminogen activator, trypsin, plasmin, or another enzyme having proteolytic activity may be used. In one method of the present invention, a compound is attached via a linker susceptible to cleavage by complement. An antibody selected from a class which can activate complement is then administered in combination with the antibody (Fab')$_2$ linker compound of the invention. The second antibody administered, thus, activates the complement cascade and releases the compound from the antibody (Fab')$_2$- linker compound conjugate at the target site. According to another embodiment of the present invention, a compound is attached via a linker susceptible to cleavage by enzymes having a proteolytic activity such as urokinase, a tissue plasminogen activator, plasmin, or trypsin or the like.

In still another embodiment, it may be necessary to construct the linker in such a way as to optimize the spacing between the compound and the antibody. This may be accomplished by use of a linker of the general structure

wherein

W is either
—NH—CH$_2$— or —CH$_2$—;
Q is an amino acid, or peptide; and
n is an integer from 0 to 20.

In still other embodiments, the linker may comprise a spacer element and a cleavable element. The spacer element serves to position the cleavable element away from the core of the antibody molecule such that the cleavable element is more accessible to the enzyme responsible for cleavage. Certain of the "branched linkers" described above may serve as spacer elements.

When the compound to be attached is a metal ion, a linker which is a compatible chelator is utilized to attach such compound to an antibody molecule. The term "a compatible chelator" is intended to mean any compound that (1) is able to donate electrons and combine by coordinate bonding with a metal ion to form structures called chelates or chelation complexes and (2) is suitable for covalent attachment to an antibody without loss of the ability to chelate metal ions or destruction of the immunospecificity of the antibody molecule. Compatible chelators include but are not limited to derivatives of diethylenetriaminepentaacetic acid, ethylenediaminetetraacetic acid (EDTA), dimercaptosuccinic acid, 2,3-dimercaptopropanesulfonic acid, metallothioein and cryptates, such as those described by Gansow et al., (1981, J. Heterocyclic Chem. 18:297).

According to the present invention, suitable compatible chelators for reaction with an oxidized carbohydrate moiety of an antibody include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the chelator, or may be introduced by suitable chemistry onto chelators not containing such groups.

For example, diethylenetriaminepentaacetic acid (DTPA) lacks an appropriate amine group for facile attachment to oxidized carbohydrate. However, chemical modification can produce a variety of suitable derivatives, such as amine-containing derivatives of mixed anhydrides of DTPA including, but not limited to p-aminoaniline-DTPA, hydrazide-DTPA, phenylhydrazide-DTPA, hydroxylamine-DTPA, semicarbazide-DTPA, thiosemicarbazide-DTPA, polyethyleneimine-DTPA, p-phenylenediamine-DTPA, DTPA mono[(4-aminophenyl)methyl]amide and amino acid-containing derivatives of DTPA, including, but not limited to α-N-DTPA-L-lysine, glycyl-tyrosyl-lysine-DTPA and L-lysine benzyl ester-DTPA.

The compound attached to the antibody compositions to prepare the antibody (Fab')$_2$ compound conjugates of the present invention is selected according to the purpose of the intended application (e.g., killing, prevention of cell proliferation, hormone therapy, target imaging, or gene therapy, etc.). Such compounds include, for example, pharmaceutical agents, toxins, fragments of toxins, alkylating agents, enzymes, antibiotics such as antibacterials, antifungals, antimycoplasmals, etc., antiviral agents, antimetabolites, antiproliferative or antineoplastic agents, hormones, neurotransmitters, DNA, radioopaque dyes, radioactive isotopes including such as I-123, I-131 as well as radioactive metal ions, metal ions, fluorogenic compounds, marker compounds, lectins and compounds which alter cell membrane permeability. Table I of European Patent Application No. 85401776.1 lists some therapeutic agents that can be used in the present invention and is incorporated herein by reference. In no way is Table I, however, meant to be an exhaustive list. Finally, a combination of compounds can be site specifically coupled to an antibody composition to prepare the antibody (Fab')$_2$ compound conjugates of the invention.

5.3. ANTIBODIES

Antibodies directed against any determinant of any antigen or hapten may be used in the present invention. While both conventional antibodies and monoclonal antibodies are suitable, monoclonal antibodies offer several advantages. Each monoclonal antibody is specific for one antigenic determinant. Additionally, a large amount of substantially homogenous monoclonal antibodies can be produced efficiently and economically using techniques known to those of skill in the art.

Classes of antibodies including IgG, IgM, and IgA can be used in the method of the present invention.

As stated above, antibodies directed against any determinant of any antigen or hapten can be employed in the reaction scheme described herein. Such determinants include, but are not limited to determinants of: tumor and malignant cells, bacterial, fungal, viral, parasitic, mycoplasmal, histocompatability, differentiation and other cell membrane antigens, pathogen surface antigens, toxins, enzymes, allergens, drugs, any biologically active molecules, etc. In some instances, a combination of monoclonal antibodies reactive with different antigenic determinants can be used.

5.4. APPLICATIONS

The aqueous soluble antibody (Fab')$_2$ compound conjugates of the present invention are advantageously useful for a variety of in vivo therapeutic and diagnostic applications.

In vivo administration may involve use of a therapeutically effective composition or a diagnostic composition comprising an aqueous soluble antibody (Fab')$_2$ conjugate in any suitable carrier, including serum or physiological saline, with or without another protein, such as human serum albumin Dosages of the antibody (Fab')$_2$ conjugates can be readily determined by one of ordinary skill and may differ depending upon the nature of the compound attached and the intended purpose of the conjugate.

The route of administration is generally parenteral, with administration via an intravenous route generally preferred.

Therapeutic applications generally involve treatment of a variety of cellular disorders by administering an effective amount of an antibody (Fab')$_2$ compound conjugate in which the compound is a therapeutic agent. The properties of the antibody (Fab')$_2$ in being immunospecific for and immunoreactive with a particular antigen or antigen determinant associated with the cellular disorder render the compositions ideally suited for delivery of the therapeutic agent to specific cells, tissues, or organs or any other in vivo site having that antigenic determinant. The properties of the antibody (Fab')$_2$ compound conjugates in having prolonged biological half-life compared to conventionally prepared antibody fragment conjugates render the present compositions especially suited for in vivo delivery of a therapeutic agent when persistence of the agent at the target site is desired.

For therapeutic applications, the compound attached to the antibody (Fab')$_2$ compositions of the invention is a therapeutic agent selected according to the intended purpose. Therapeutic agents such as those described above in Section 5.2 can be employed. In some instances, the therapeutic agent is a radioactive isotope such as I-131, Yttrium-90, Copper-67, Rhenium-186, Rhenium-188, Iron-59, Bismuth-212, Lead-212, etc.

As used in this application the term "cellular disorder" is intended to include all neoplasms, such as cancers, adenomas, hyperplasias, etc.; certain immunological disorders, including graft-versus-host diseases (e.g., after bone marrow transplantation); immune suppressive disorders, (e.g., acquired immune deficincy syndrome (AIDS), after kidney or bone marrow transplantation); cardiovascular diseases such as those associated with the formation of atherosclerotic plaques, etc,; infections induced by viral, bacterial, fungal, mycoplasmal, or parasitic agents, etc.

Diagnostic applications generally involve imaging of specific tissues or cellular disorders by administration of a sufficient amount of an antibody (Fab')$_2$ compound conjugate to enable detection or localization of the conjugate at the target tissue in an appropriate time frame. For diagnostic imaging purposes, the antibody (Fab')$_2$ compound conjugates may comprise a compound which is a nonmetallic radioactive isotope such as I-123 coupled via a linker according to the method of the invention. Alternatively, the antibody (Fab')$_2$ compound conjugates for diagnostic imaging purposes comprise a compound which is a metal ion attached to a linker which is a compatible chelator according to the method of the invention. Thus, the compositions for diagnostic applications are preferably antibody (Fab')$_2$ chelator metal ion complexes. Dosages and other aspects of administration of the complexes are readily determined by one of ordinary skill in the art.

A wide variety of metal ions are suited for preparing the antibody (Fab')$_2$ metal ion complexes including radioisotopes such as Indium-111, Technetium-99m, Copper-67, etc., positron emitting metal ions such as Scandium-43, Scandium-47, Iron-52, Cobalt-55, Gallium 68; and nonradioactive paramagnetic metal ions such as Iron-54; Iron-56, Iron-57, Iron-58, Gadolium-57, Manganese-55, etc which are detectible by nuclear magnetic resonance spectroscopy.

Tissues and cellular disorders which may be imaged include any solid neoplasms, certain organs such as lymph nodes, parathyroids, spleen and kidney, sites of inflamation or infection (e.g. macrophages at such sites), mycocardial infarction or thromboses, (neoantigenic determinants or fibrin, platelets), etc.

5.5. ADVANTAGES OF ANTIBODY (FAB,)$_2$ COMPOUND CONJUGATES

The antibody (Fab')$_2$ compound conjugates of the present invention in which a compound is attached, either directly or via a linker, site specifically to a carbohydrate moiety of an antibody which is located outside the antigen binding region of the antibody, possess substantially the same immunospecificity as the unconjugated whole antibody molecule. Moreover, when administered in vivo the antibody (Fab')$_2$ compound conjugates of the invention persist longer in the circulation and are not rapidly excreted, for example through the kidney, liver or spleen, compared to analogous (Fab')$_2$ conjugates prepared by conventional methods using preformed (Fab')$_2$ fragments. The longer persistence or residence time in the body and the specificity of the conjugates for the intended target antigenic site provide significant advantages when the antibody (Fab')$_2$ conjugates are used for targeted in vivo delivery systems for therapeutic and/or diagnostic applications.

The following Examples are presented for purposes of illustration only and not by way of limitation on the scope of the present invention.

6. ENHANCED BIODISTRIBUTION OF B72.3 ANTIBODY (FAB')$_2$-GYK-DTPA-$^{III}$IN

The following experiments demonstrate that a radiolabeled antibody (Fab')$_2$ fragment-chelator metal ion complex prepared according to the method of the invention has significantly enhanced biodistribution compared to an analogous conventional complex when administered to experimental animals.

The antibody employed in these experiments was a monoclonal antibody (IgG$_1$) reactive with human breast and colon cancer obtained from hybridoma cell line ATCC No. B72.3 (hereinafter "B72.3 antibody") described in U.S. Pat. No. 4,522,918 issued to Schlom et al. (See, Nuti et al., 1982, Int. J. Cancer 29: 539–45).

In one series of experiments, a B72.3 antibody (Fab')$_2$-chelator metal ion complex was prepared according to the method of the invention as follows:

METHOD A (1) An antibody-chelator intermediate was formed using the method of Rodwell et al., 1986, Proc. Nat'l Acad. Sci. USA 83:2632–36.

Briefly, the carbohydrate moieties of the antibodies were oxidized by incubation in the dark with 10–30 mM NaIO$_4$ in phosphate buffered saline (0.15 M NaCl/0.01M sodium phosphate; PBS) at pH 6.0 in ice for 1 hour. The antibodies were purified using a Sephadex ® G-25 column equilibrated with PBS at pH 6.0.

The antibodies having oxidized carbohydrate moieties were then incubated with a derivative of the chelator diethylentriaminepentaacetic acid (DTPA), i.e., glycyltyrosyllysyl diethylentriaminepentaacetic acid (GYK-DTPA) at a one-thousand molar excess of GYK-DTPA for 1 hour at room temperature. Sodium cyanoborohydride (Aldrich Chemical Co. Inc., Milwaukee, WI) was added to a final concentration of 10 mM. The reaction mixture was incubated for an additional 4 hours and then either dialyzed at 4° C. against several changes of PBS or passed through a Sephadex ® G-50 gel column.

(2) The B72.3-GYK-DTPA antibody-chelator intermediate was then digested with pre-activated bromelain according to the method generally described by Parham (1983, J. Immunol. 131:2895–02) to form a B72.3 (Fab')$_2$-GYK-DTPA intermediate. The bromelain (1 mg/ml) was activated by incubation for about 1 hour at room temperature with 50 mM cysteine in acetate buffer (100 mM acetate, pH 5.5) containing 3 mM EDTA. The cysteine was removed from the activation mixture by desalting through Sephadex ® G-25. B72.3 (Fab')$_2$-GYK-DTPA was then digested with activated bromelain (5% based on the weight of the antibody-linker intermediate) in acetate buffer. The digestion was monitored using size exclusion chromatography (SEC) high performance liquid chromatography (HPLC). The B72.3 (Fab')$_2$ GYK-DTPA obtained was purified using a Protein A column (Affi-Gel Protein A, BioRad Laboratories, Richmond, CA), and then using a gel filtration column (AcA44, IBF Biotechnics, Savage, MD) in PBS, pH 6.0. The product was analyzed using sodium dodecyl sulfate polyacrylamide gel electrophoresis (SDS-PAGE) and HPLC-(SEC) to identify the B72.3 (Fab')$_2$ GYK-DTPA having a molecular weight of about 100,000 daltons.

(3) A B72.3 (Fab')$_2$ metal ion complex was then formed by incubating the B72.3 (Fab')$_2$-GYK-DTPA intermediate with lllInCl (1 mCi) (New England Nuclear, Boston, MA) in PBS pH 6.0 for about 1 hour at 37° C. The B72.3 (Fab')$_2$-GYK-DTPA-$^{111}$In formed was separated from free lllIn by HPLC using a TSK-G3000SW column.

In another series of experiments, a B72.3 antibody (Fab')$_2$-chelator metal ion complex was prepared according to the invention as follows:

METHOD B (1) An antibody-chelator intermediate was formed as described above using the method of Rodwell et al., supra.

(2) An antibody-chelator metal ion complex was then prepared by incubating (100 μg) of the B72.3-GYK-DTPA intermediate with $^{111}$InCl$_3$ (1 mCi) (New England Nuclear, Boston, MA) in PBS, pH 6.0 for 1 hour at 37° C.

(3) The B72.3-GYK-DTPA-$^{111}$In complex was then digested with pre-activated bromelain as described above except that EDTA was omitted from the buffer. The B72.3 (Fab')$_2$ GYK-DTPA $^{111}$In was purified by passage through an TSK-G3000 SW HPLC column.

An analogous conventional B72.3 (Fab')$_2$ chelator metal ion complex was also prepared as follows:

(1) B72.3 antibody was digested with preactivated bromelain according to the general method of Parham, supra, to form B72.3 (Fab')$_2$ fragments. The B72.3 (Fab')$_2$ fragments were separated from the Fc fragments and any residual whole antibody by chromatography using Protein A and a gel filtration column as described above.

(2) A B72.3 (Fab')$_2$-GYK-DTPA intermediate was then formed by oxidizing the carbohydrate moiety of the B72.3 (Fab')$_2$ fragment according to the method of Rodwell et al., supra, and reacting the aldehyde group so formed with a reactive amine of the chelator derivative GYK-DTPA. The B72.3 (Fab')$_2$-GYK-DTPA intermediate was then stabilized by incubation with sodium cyanoborhydride as described above;

(3) The B72.3 (Fab')$_2$-GYK-DTPA intermediate (100 μg) was incubated with $^{111}$InCl$_3$ (1 mCi) (New England Nuclear, Boston, MA) in PBS pH 6.0 for 1 hour at 37° C. The B72.3 (Fab')$_2$-GYK-DTPA-$^{111}$In complex thus formed was purified by HPLC using a TSK-G30008W column.

The B72.3-(Fab')$_2$-GYK-$^{111}$In complexes prepared according to the present invention and according to conventional methods were analyzed using size-exclusion chromatography (SEC) HPLC. SEC-HPLC of both the types of complexes showed that these complexes were of substantially the same size and homogenous.

A whole B72.3 antibody -GYK-DTPA-$^{111}$In complex was also prepared for comparison, as described above, without enzymatic digestion.

The biodistribution of B72.3 (Fab')$_2$ metal ion complexes prepared according to the present invention and according to conventional methods, as well as whole B72.3 metal ion complexes, was evaluated following in vivo administration to experimental animals.

In one series of experiments, female nude (nu/nu) mice (Taconic Farms, Germantown, NJ) bearing human tumor xenografts were obtained by subcutaneous injection with about 1×10$^6$ LS174T (ATCC) human colon adenocarcinoma cells (0.2 ml) in the left rear flank. When the tumors were about 10-15 mm ×15-20 mm, 200 μl of the B72.3 (Fab')$_2$ complex (13 μg) of the present invention, and of the conventional B72.3 (Fab')$_2$-GYK-DTPA-$^{111}$In complexes (13 μg) were each injected intravenously into 3 tumor-bearing and 3 non-tumor bearing nude (nu/nu) (control) animals. Whole B72.3-GYK-DTPA-$^{111}$In complexes (13 μg) were similarly administered into 2 tumorbearing and 3 non-tumor bearing animals for comparison. Animals were sacrificed and dissected at 4 days postinjection to obtain quantitative biodistribution data. At the time of dissection, tumors averaged 1.12±0.59 g. Results obtained in tumor-bearing animals are illustrated in Table 1 and in non-tumor bearing animals in Table 2.

TABLE 1

BIODISTRIBUTION OF B72.3(FAB')$_2$ GYK-DTPA $^{111}$IN COMPLEXES IN TUMOR BEARING ANIMALS

| Tissue Organ:Blood Ratio | B72.3 (Fab')$_2$ Complexes Of the Invention[a] | Conventional B72.3 (Fab')$_2$ Complexes[a] | Whole B72.3 Complexes[b] |
|---|---|---|---|
| Lung | 1.04 ± 0.58 | 2.81 ± 0.22 | 0.77 ± 0.19 |
| Spleen | 1.26 ± 0.72 | 6.34 ± 0.67 | 0.86 ± 0.21 |
| Liver | 2.52 ± 1.21 | 27.57 ± 4.59 | 1.89 ± 0.91 |
| Kidneys | 11.80 ± 5.70 | 168.96 ± 41.18 | 1.73 ± 0.73 |
| Tumor | 4.93 ± 3.24 | 6.18 ± 1.99 | 7.08 ± 3.07 |
| Muscle | 0.98 ± 1.33 | 1.40 ± 0.26 | 0.22 ± 0.04 |
| Tissue % Injected Dose/gram | | | |
| Blood | 2.46 ± 2.05 | 0.09 ± 0.02 | 3.37 ± 2.11 |
| Lung | 1.81 ± 0.30 | 0.24 ± 0.05 | 2.41 ± 0.98 |
| Spleen | 2.24 ± 0.53 | 0.54 ± 0.09 | 2.67 ± 1.09 |
| Liver | 4.59 ± 1.02 | 2.33 ± 0.27 | 5.42 ± 0.91 |
| Kidneys | 21.60 ± 6.23 | 14.37 ± 3.98 | 4.88 ± 0.52 |
| Tumor | 8.39 ± 2.03 | 0.52 ± 0.14 | 20.63 ± 4.55 |
| Muscle | 1.40 ± 1.47 | 0.12 ± 0.02 | 0.70 ± 0.34 |
| Isotope Half-Life[c] | 3.3 ± 0.1 | 0.9 ± 0.1 | 6.1 ± 1.2 |

[a]Values represent $\bar{x}$ ± SD, N = 3.
[b]Values represent $\bar{x}$ ± SD, N = 2.
[c]Half-life (days) determinations were made based on whole animal dose-calibrator measurements each day of the study, beginning just after injection and ending just before dissection.

TABLE 2

BIODISTRIBUTION OF B72.3(FAB')$_2$ GYK-DTPA $^{111}$IN COMPLEXES IN NON-TUMOR BEARING ANIMALS[a]

| Tissue Organ:Blood Ratio | B72.3 (Fab')$_2$ Complexes Of the Invention | Conventional B72.3 (Fab')$_2$ Complexes | Whole B72.3 Complexes |
|---|---|---|---|
| Lung | 1.05 ± 0.19 | 3.07 ± 1.30 | 0.68 ± 0.16 |
| Spleen | 1.15 ± 0.43 | 7.24 ± 2.94 | 0.46 ± 0.10 |
| Liver | 3.42 ± 2.32 | 25.29 ± 4.36 | 0.81 ± 0.65 |
| Kidneys | 11.91 ± 2.76 | 195.31 ± 107.35 | 0.65 ± 0.18 |
| Muscle | 2.01 ± 1.81 | 1.70 ± 0.65 | 0.11 ± 0.04 |
| Tissue % Injected Dose/gram | | | |
| Blood | 1.99 ± 0.35 | 0.08 ± 0.03 | 8.49 ± 3.61 |
| Lung | 2.11 ± 0.55 | 0.24 ± 0.04 | 5.43 ± 1.57 |
| Spleen | 2.30 ± 0.90 | 0.55 ± 0.08 | 3.63 ± 0.82 |
| Liver | 6.68 ± 4.52 | 2.03 ± 0.26 | 7.09 ± 3.86 |
| Kidneys | 23.32 ± 4.72 | 14.19 ± 4.98 | 4.98 ± 0.59 |
| Muscle | 3.59 ± 2.84 | 0.13 ± 0.03 | 0.85 ± 0.11 |
| Isotope | 3.1 ± 0.2 | 0.8 ± 0.2 | 5.8 ± 0.9 |

TABLE 2-continued

BIODISTRIBUTION OF B72.3(FAB')₂ GYK-DTPA ¹¹¹IN COMPLEXES IN NON-TUMOR BEARING ANIMALS[a]

| Tissue Organ:Blood Ratio | B72.3 (Fab')₂ Complexes Of the Invention | Conventional B72.3 (Fab')₂ Complexes | Whole B72.3 Complexes |
|---|---|---|---|
| Half-Life[b] | | | |

[a]Values represent $\bar{X} \pm SD$, N = 3.
[b]Half-life (days) determinations were made based on whole animal dose-calibrator measurements each day of the study, beginning just after injection and ending just before dissection.

As clearly demonstrated, the mean residence time expressed as the Isotope Half-life of the B72.3 (Fab')₂ metal ion complex of the invention was significantly longer than that of analogous conventionally prepared conjugates. Additionally the biodistribution pattern of the two differently prepared antibody (Fab')₂ conjugates differed significantly. In particular, the B72.3 (Fab')₂ conjugate of the invention localized much more specifically to the target tumor site and less so to other non-target organs (see Tissue Organ: Blood Ratios).

In another series of experiments, female nude mice (nu/nu) bearing human LS174T tumor xenografts were obtained as described above. One or two tumor-bearing animals and two or three non-tumor bearing animals were injected intraperitoneally with 300 μl of B72.3 (Fab')₂ GYK-DTPA-¹¹¹In of the present invention prepared by Method B above or 300 μl (8 μg) of a whole B72.3 GYK-DTPA-¹¹¹In complex (3 μg) in PBS. Three days post-injection, the animals were sacrificed and dissected. At the time of dissection, tumor weights averaged 1.13±0.54 g. Normal Balb/c mice served as non-tumor bearing controls.

Results are illustrated in Table 3 for tumor-bearing and in Table 4 for non-tumor bearing animals.

TABLE 3

BIODISTRIBUTION OF B72.3(FAB')₂ GYK-DTPA ¹¹¹IN COMPLEXES IN TUMOR BEARING ANIMALS

| Tissue Organ:Blood Ratio | B72.3 (Fab')₂ Complexes Of the Invention[a] | Whole B72.3 Complexes[b] |
|---|---|---|
| Lung | 0.74 ± 0.05 | 0.69 |
| Spleen | 0.44 ± 0.02 | 0.95 |
| Liver | 0.46 ± 0.04 | 1.41 |
| Kidneys | 11.44 ± 1.20 | 2.03 |
| Tumor | 1.40 ± 0.02 | 5.11 |
| Muscle | 0.26 ± 0.04 | 0.27 |
| Tissue % Injected Dose/gram | | |
| Blood | 2.96 ± 0.29 | 4.82 |
| Lung | 2.08 ± 0.06 | 3.32 |
| Spleen | 1.32 ± 0.06 | 4.60 |
| Liver | 1.36 ± 0.02 | 6.78 |
| Kidneys | 33.74 ± 1.01 | 9.75 |
| Tumor | 4.14 ± 0.48 | 24.64 |
| Muscle | 0.78 ± 0.05 | 1.29 |
| Isotope Half-Life | 2.6 ± 0 days | 9.5 days |

[a]Values represent $\bar{X} \pm S.D.$, N = 2.
[b]N = 1.

TABLE 4

BIODISTRIBUTION OF B72.3(FAB')₂ GYK-DTPA ¹¹¹IN COMPLEXES IN NON-TUMOR BEARING ANIMALS

| Tissue Organ:Blood Ratio | B72.3 (Fab')₂ Complexes Of the Invention[a] | Whole B72.3 Complexes[b] |
|---|---|---|
| Lung | 0.79 ± 0.03 | 0.06 ± 0.02 |
| Spleen | 0.53 ± 0.07 | 0.48 ± 0.01 |
| Liver | 0.84 ± 0.16 | 0.66 ± 0.06 |
| Kidneys | 11.08 ± 0.87 | 0.92 ± 0.08 |
| Muscle | 0.10 ± 0.02 | 0.11 ± 0.01 |
| Tissue % Injected Dose/gram | | |
| Blood | 5.36 ± 0.38 | 21.17 ± 0.27 |
| Lung | 4.23 ± 0.22 | 12.73 ± 0.59 |
| Spleen | 2.81 ± 0.32 | 10.18 ± 0.27 |
| Liver | 3.45 ± 0.99 | 13.83 ± 1.56 |
| Kidneys | 59.58 ± 7.16 | 19.48 ± 1.95 |
| Muscle | 0.94 ± 0.04 | 2.32 ± 0.16 |
| Isotope Half-Life | 3.3 ± 0.3 days | 13.9 ± 2.4 days |

[a]Values represent $\bar{X} \pm SD$, N = 3.
[b]Values represent $X \pm SD$, N = 2.

The data in Tables 3 and 4 confirm the results presented in Tables 1 and 2. The biodistribution of B72.3 (Fab')₂-GYK-DTPA-¹¹¹In complexes prepared according to the method of the invention was significantly different from that of analogous complexes prepared according to the conventional method. At 4 days post-injection of complexes of the invention, about 8% of the injected complex was localized at the tumor target site, whereas at the same time only about 0.5% of the injected conventionally prepared complex was localized at the tumor site. Moreover, the conventionally prepared (Fab')₂ complexes were excreted very rapidly and showed high localization at the kidney and liver prepared according to the method of the invention persisted in the circulation about three times as long as conventionally prepared complexes and showed significantly less localization at the kidney and liver.

7. IN VITRO BINDING ACTIVITY OF B72.3 AND B72.3 (Fab')₂ COMPOSITIONS

The following experiment shows that an antibody (Fab')₂-linker intermediate prepared according to the method of the invention and an antibody (Fab')₂ fragment prepared using a conventional method had substantially the same binding activity when measured using an in vitro binding assay. The experiment further shows that the binding activity of the (Fab')₂ compositions was substantially the same as that of the unconjugated antibody.

A whole B72.3 linker intermediate, (i.e. B72.3-GYK-DTPA) and a B72.3 (Fab')₂ linker intermediate (i.e. B72.3 (Fab')₂-GYK-DTPA were prepared as described in Section 6 above. A conventional B72.3 (Fab')₂ fragment was also prepared as described above.

An enzyme-linked immunosorbent assay (ELISA) was used to assess the in vitro binding activity of the antibody and (Fab')₂ fragment compositions as follows: The assays were performed using microtiter plates on which were grown and then fixed human LS174T cells which contain the TAG-72 antigen for which B72.3 antibody is specific. The antibody or (Fab')₂ fragment compositions to be tested were serially diluted 1:2 on the plates from 10 μg/ml to 0.04 μg/ml (corresponding to 67 nM/l to 0.26 nM/l for whole antibody and 100 nM/l to 0.39 nM/l for (Fab') fragment, respectively). The bound antibody or (Fab')₂ fragment compositions were detected using anti-mouse IgG-Fab conjugated to peroxidase (Jackson Immunoresearch). The substrate used was tetramethylbenzidine. Results obtained are graphically illustrated in FIG. 1 (A and B).

As demonstrated in FIG. IA, both the B72.3 antibody (Fab')$_2$ composition prepared according to the method of the invention and the conventional B72.3 (Fab') had substantially the same specific binding activity when measured using an in vitro ELISA binding assay. Moreover, as demonstrated in FIG. IB, the specific binding activity of whole native B72.3 antibody and B72.3 antibody having a linker moiety site specifically attached to an oxidized carbohydrate moiety also has substantailly the same binding activity as the (Fab')$_2$ fragments using the in vitro ELISA assay. A control IgG$_1$ antibody MOPC-21 had no activity in the ELISA assay (data not shown).

8. CARBOHYDRATE ANALYSIS OF A B72.3 (FAB')$_2$ FRAGMENT

The following experiment was performed to evaluate the carbohydrate moieties of the whole B72.3 antibody molecule and B72.3 (Fab')$_2$ fragments analogous to those formed in the reaction scheme of the present invention.

B72.3 (Fab')$_2$ fragments were obtained by digesting an aliquot of B72.3 antibody with activated bromelain as described in Section 6 above. The carbohydrate moieties of both the whole B72.3 antibody molecule and the B72.3 (Fab')$_2$ fragments were analyzed using three separate hydrolyses as follows:
  (1) amino sugars such as glucosamine (Glc-Am) and galactosamine (Gal-Am) were analyzed after hydrolysis in 6N HCl at 100° C. for 3 hours;
  (2) neutral sugars such as galactose, mannose and fucose were analyzed after hydrolyis in 4 M trifluoroacetic acid (TFA) at 100° C. for 2 hours; and
  (3) sialic acid was analyzed after hydrolysis in 20 mM H$_2$SO$_4$ at 80° C. for 1 hour.

The neutral sugars were converted to amino-containing forms prior to analysis. The hydrolyzed samples were analyzed by cation-exchange HPLC, using an orthophthaldehyde reactor and fluorescence detector. Results are graphically illustrated in FIG. 2.

As shown in FIG. 2, the carbohydrate moieties of B72.3 (Fab')$_2$ fragments comprise galactosamine, galactose, and sialic acid residues. Glucosamine, mannose and fucose residues as well as an extra sialic acid residue present in the whole antibody molecule are not found in the B72.3 (Fab')$_2$ fragment. The composition of the carbohydrate moieties on the (Fab')$_2$ fragment indicates that it is an 0-linked carbohydrate moiety.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. such modifications are also intended to fall within the scope of the appended claims.

We claim:

1. A method for preparing an antibody fragment compound conjugate, comprising: reacting a soluble antibody-compound conjugate, which comprises an antibody attached to a compound by a covalent bond to an oxidized carbohydrate of the antibody located outside the antigen binding region of said antibody, with an activated thiol protease enzyme to form an (Fab')$_2$-compound conjugate, characterized by (a) substantially the same immunospecificity as the unconjugated antibody and (b) aqueous solubility such that the (Fab')$_2$.-compound conjugate is suitable for in vivo administration.

2. The method according to claim 1, in which the thiol protease is bromelain, papain, chymopapain or ficin.

3. The method according to claim 1, in which the thiol protease is activated by reacting it with cysteine or a sulfhydryl reducing agent selected from the group consisting of dithiothreitol, mercaptoethanol and mercaptoethylamine.

4. The method according to claim 1, in which the antibody-compound conjugate is formed by a method, comprising:
  (a) reacting an antibody with an oxidizing agent to form an aldehyde group in a carbohydrate moiety of the antibody located outside the antigen binding region of the antibody; and
  (b) reacting the aldehyde group of the resultant oxidized carbohydrate moiety of the antibody with an amine group of a compound selected from the group consisting of primary amine, secondary amine, hydrazine, hydrazide, hydroxylamine, phenylhydrazine, semicarbazide and thiosemicarbazide groups, to form a soluble antibody-compound conjugate being characterized by (i) substantially the same immunospecificity as the unconjugated antibody and (ii) aqueous solubility such that the antibody compound conjugate is suitable for in vivo administration.

5. The method according to claim 4, in which the oxidizing agent is an enzyme.

6. The method according to claim 4, in which the oxidizing agent is an oxygen acid.

7. A method for preparing an antibody fragment compound conjugate, comprising:
  (a) reacting an antibody-linker intermediate, which comprises a linker attached via a covalent bond to an oxidized carbohydrate moiety of an antibody, in which the carbohydrate moiety is located outside the antigen binding region of the antibody, in which the antibody-linker intermediate is characterized by (i) substantially the same immunospecificity as the unconjugated antibody and (ii) aqueous solubility such that the antibody-linker intermediate is suitable for in vivo administration, with an activated thiol protease to form a soluble (Fab')$_2$-linker intermediate; and
  (b) attaching the linker portion of the (Fab')$_2$-linker intermediate either by a covalent bond or a coordinate bond to a compound to form a soluble (Fab')$_2$-linker-compound conjugate characterized by (i) substantially the same immunospecificity as the unconjugated antibody and (ii) aqueous solubility such that the (Fab')$_2$-linker-compound conjugate is suitable for in vivo administration.

8. The method according to claim 7, in which the thiol protease is bromelain, papain, chymopapain or ficin.

9. The method according to claim 7, in which the antibody-linker intermediate is formed by a method, comprising:
  (a) reacting an antibody with an oxidizing agent to form an aldehyde group in a carbohydrate moiety of the antibody located outside the antigen binding region of the antibody; and (b) reacting the aldehyde group of the resultant oxidized carbohydrate moiety of the antibody with an amine group of a linker selected from the group consisting of primary amine, secondary amine, hydrazine, hydrazide, hydroxylamine, phenylhydrazine, semicarbazide and thiosemicarbaozide groups, to form a soluble antibody-linker intermediate being characterized by (i) substantially the same immunospecificity as the unconjugated antibody and (ii) aqueous solubility such that the antibody-linker intermediate is suitable for in vivo administration.

10. The method according to claim 9, in which the oxidizing agent is an enzyme.

11. The method according to claim 9, in which the oxidizing agent is an oxygen acid.

12. A method for preparing an antibody fragment-compound conjugate, comprising: reacting a soluble antibody-linker-compound conjugate, which comprises a linker-compound moiety attached via a covalent bond to an oxidized carbohydrate moiety of an antibody, in which the carbohydrate moiety is located outside the antigen binding region of the antibody, and in which the antibody-linker-compound conjugate is characterized by (a) substantially the same immunospecificity as the unconjugated antibody and (b) aqueous solubility such that the antibody-linker-compound conjugate is suitable for in vivo administration, with an activated thiol protease to form a soluble antibody F(ab')$_2$-linker compound conjugate, characterized by (i) substantially the same immunospecificity as the unconjugated antibody and (ii) aqueous solubility such that the antibody F(ab')$_2$-linker compound conjugate is suitable for in vivo administration.

13. The method according to claim 12, in which the thiol protease is bromelain, papain, chymopapain or ficin.

14. The method according to claim 12, in which the antibody-linker-compound conjugate is formed by a method, comprising: covalently or coordinately attaching a linker portion of an antibody-linker intermediate which comprises a linker covalently attached to an oxidized carbohydrate moiety of an antibody, in which the carbohydrate moiety is located outside the antigen binding region of the antibody, to a compound to form a soluble antibody-linker-compound conjugate being characterized by (a) substantially the same immunospecificity as the unconjugated antibody and (b) aqueous solubility such that the antibody-linker-compound conjugate is suitable for in vivo administration.

15. The method according to claim 12, in which the antibody-linker-compound conjugate is formed by a method, comprising:

(a) reacting an antibody with an oxidizing agent to form an aldehyde group in a carbohydrate moiety of the antibody, in which the carbohydrate moiety is located outside the antigen binding region of the antibody;

(b) reacting the aldehyde group of the resultant oxidized carbohydrate moiety of the antibody with an amine group of a linker containing an amine group selected from the group consisting of primary amine, secondary amine, hydrazine, hydrazide, hydroxylamine, phenylhydrazine, semicarbazide and thiosemicarbazide groups, to form an antibody-linker intermediate; and (c) covalently or coordinately attaching a compound to the linker portion of the antibody-linker intermediate to form an antibody-linker-compound conjugate being characterized by (i) substantially the same immunospecificity as the unconjugated antibody and (ii) aqueous solubility such that the antibody-linker-compound conjugate is suitable for in vivo administration.

16. The method according to claim 12, in which the antibody-linker-compound conjugate is formed by a method, comprising: covalently attaching an amine group of a linker moiety of a linker-compound intermediate containing a reactive amine group selected from the group consisting of primary amine, secondary amine, hydrazine, hydrazide, hydroxylamine, phenylhydrazine, semicarbazide and thiosemicarbazide group to an oxidized carbohydrate moiety of an antibody to form an antibody-linker-compound being characterized by (a) substantially the same immunospecificity as the unconjugated antibody and (b) aqueous solubility such that the antibody-linker-compound conjugate is suitable for in vivo administration.

17. The method according to claim 12, in which the antibody-linker compound conjugate is formed by a method, comprising:

(a) reacting an antibody with an oxidizing agent to form an aldehyde group in a carbohydrate moiety of the antibody, in which the carbohydrate moiety is located outside the antigen binding region of the antibody;

(b) reacting the aldehyde groups of the resultant oxidized carbohydrate moiety of the antibody with an amine group of a linker-compound intermediate containing an amine group selected from the group consisting of primary amine, secondary amine, hydrazine, hydrazide, hydroxylamine, phenylhydrazine, semicarbazide and thiosemicarbazide to form an antibody-linker-compound conjugate, being characterized by (a) substantially the same immunospecificity as the unconjugated antibody and (b) aqueous solubility such that the antibody-linker-compound conjugate is suitable for in vivo administration.

18. The method according to claim 1, 7 or 12, in which the antibody is a monoclonal antibody.

19. The method according to claim 7 or 12, in which the linker is a compatible chelator selected from the group consisting of amine-containing derivatives of diethylenetriaminepentaacetic acid, ethylenediaminetetraacetic acid, dimercaptosuccinic acid, 2,3-dimercaptopropanesulfonic acid, metallothioein and cryptates.

20. The method according to claim 7 or 12, in which the linker is selected from the group consisting of p-aminoanaline-diethylenetriaminepentaacetic acid, hydrazidediethylenetriaminepentaacetic acid, phenylhydrazidediethylenetriaminepentaacetic acid, hydroxylaminediethylenetriaminepentaacetic acid, semicarbazidediethylenetriaminepentaacetic acid, thiosemicarbazidediethylenetriaminepentaacetic acid, polyethyleneiminediethylenetriaminepentaacetic acid, p-phenylenediaminediethylenetriaminepentaacetic acid, diethylenetriaminepentaacetic acid mono[(4-aminophenyl)methyl]amide, α-N-diethylenetriaminepentaacetic acid-L-lysine, glycyl-tyrosyl-lysine-diethylenetriaminepentaacetic acid and L-lysine benzyl ester -diethylenetriaminepentaacetic acid.

21. An antibody fragment-compound conjugate, comprising: a soluble F(ab')$_2$ -compound conjugate prepared by a method which comprises: reacting a soluble antibody-compound conjugate, comprising an antibody attached to a compound by a covalent bond to an oxidized carbohydrate of the antibody, located outside the antigen binding region of the antibody, with an activated thiol protease enzyme to from F(ab')$_2$-compound conjugate, in which the antibody F(ab')$_2$-compound conjugate is characterized by (a) substantially the same immunospecificity as the unconjugated antibody and (b) aqueous solubility such that the F(ab')$_2$-compound conjugate is suitable for in vivo administration.

22. An antibody fragment-compound conjugate, comprising: a soluble F(ab')$_2$-compound conjugate prepared by a method which comprises:
  (a) reacting an antibody-linker intermediate which comprises a linker attached via a covalent bond to an oxidized carbohydrate moiety of an antibody, in which the carbohydrate moiety is located outside the antigen binding region of the antibody and in which the antibody-linker intermediate is characterized by (i) substantially the same immunospecificity as the unconjugated antibody and (ii) aqueous solubility such that the antibody-linker intermediate is suitable for in vivo administration, with an activated thiol protease enzyme to form a soluble F(ab')$_2$ linker intermediate; and
  (b) attaching the linker portion of the F(ab')$_2$-linker intermediate either by a covalent or coordinate bond to a compound to form a F(ab')$_2$-linker compound conjugate being characterized by (i) substantially the same immunospecificity as the unconjugated antibody and (ii) aqueous solubility such that the F(ab')$_2$-linker -compound conjugate is suitable for in vivo administration.

23. An antibody fragment-compound conjugate, comprising: a soluble F(ab')$_2$-compound conjugate prepared by a method which comprises: reacting a soluble antibody-linker-compound conjugate, which comprises a linker-compound moiety attached via a covalent bond to an oxidized carbohydrate moiety of an antibody, in which the carbohydrate moiety is located outside the antigen binding region of the antibody and in which the antibody-linker-compound conjugate is characterized by (a) substantially the same immunospecificity as the unconjugated antibody and (b) aqueous solubility such that the antibody-linker-compound conjugate is suitable for in vivo administration, with an activated thiol protease to form a soluble F(ab')$_2$ -linker-compound, being characterized by (a) substantially the same immunospecificity as the unconjugated antibody and (b) aqueous solubility such that the antibody-linker-compound conjugate is suitable for in vivo administration.

24. A method for in vivo imaging of a specific tissue, comprising:
  (a) administering to an animal or a human an effective amount of an aqueous soluble antibody F(ab')$_2$-compound conjugate according to claim 21, 22 or 23 in which the F(ab')$_2$-compound conjugate is immunoreactive with and immunospecific for an antigenic determinant of the specific tissue and non-immunospecific for non-specific tissue and in which the antigenic determinant is not found in substantial amounts in non-specific tissue; and
  (b) detecting the F(ab')$_2$-compound conjugate localized at the specific tissue.

* * * * *